United States Patent
Maedera et al.

[11] Patent Number: 5,611,971
[45] Date of Patent: Mar. 18, 1997

[54] PRODUCTION OF MICROCAPSULES OF WATER-SOLUBLE DRUGS

[75] Inventors: Koichi Maedera, Suita; Masuhisa Hori, Amagasaki; Tomomichi Futo, Ikeda, all of Japan

[73] Assignee: Takeda Chemical Industries, Ltd., Osaka, Japan

[21] Appl. No.: 102,790

[22] Filed: Aug. 6, 1993

[30] Foreign Application Priority Data

Aug. 7, 1992 [JP] Japan ................................. 4-211462

[51] Int. Cl.$^6$ .............................. B01J 13/02; B01J 13/04
[52] U.S. Cl. ............................................. 264/4.1; 264/4.6
[58] Field of Search ........................... 264/4.6, 4.1

[56] References Cited

U.S. PATENT DOCUMENTS

| | | | |
|---|---|---|---|
| 3,703,576 | 11/1972 | Kitajima et al. | 424/495 |
| 3,891,570 | 6/1975 | Fukushimal et al. | 252/316 |
| 4,954,298 | 9/1990 | Yamamoto et al. | 264/4.6 |

FOREIGN PATENT DOCUMENTS

| | | |
|---|---|---|
| 0145240 | 6/1985 | European Pat. Off. . |
| 0461630 | 12/1991 | European Pat. Off. . |
| 0467389 | 1/1992 | European Pat. Off. . |
| 2169316 | 9/1973 | France . |
| 60-100516 | 6/1985 | Japan . |
| 1156912 | 6/1989 | Japan . |
| 446115 | 2/1992 | Japan . |
| 446116 | 2/1992 | Japan . |
| 4123127 | 4/1992 | Japan . |
| 597660 | 4/1993 | Japan . |
| 07196479 | 8/1995 | Japan . |
| 9204891 | 4/1992 | WIPO . |

OTHER PUBLICATIONS

K. Thoma et al., "beziehungen sqischen herstellungeparametern und pharmazcutisch–technologischen anforderungen an biodegradierbare mikropartikeln" DIE PHARMAZIE, vol. 47, No. 2, Feb. '92, pp. 115–119.

*Primary Examiner*—Nathan M. Nutter
*Attorney, Agent, or Firm*—Foley & Lardner

[57] ABSTRACT

There is provided a process for producing microcapsules of a water-soluble drug by in-water drying process, which comprises carrying out the process in the presence of an osmotic pressure adjustor present in the external aqueous phase. This process improves the drug take up into microcapsules.

21 Claims, No Drawings

PRODUCTION OF MICROCAPSULES OF WATER-SOLUBLE DRUGS

FIELD OF THE INVENTION

The present invention relates to a process for producing microcapsules of water-soluble drugs.

BACKGROUND OF THE INVENTION

JP-A 4-46115 and JP-A 4-46116 (EP-A-461630) disclose a process for producing microspheres of water-soluble drugs by oil-in-water (O/W) type in-liquid drying process wherein the solvent of the oil phase is composed of at least one water-insoluble solvent and at least one water-miscible solvent as well as preparation of microspheres wherein an aliphatic acid salt is added to the oil phase. Further, the abstract of the 112th Annual Meeting of the Pharmaceutical Society of Japan (IV, p. 86) discloses microspheres obtained from an O/W type emulsion of a water-soluble drug by dissolving a high molecular polymer in the first solvent to disperse the drug, (2) adding the second solvent for homogeneous dissolution, and then (3) subjecting the resulting solution to O/W type in-liquid drying.

Journal Microencapsulation, 1988, Vol. 5, No. 2, p. 147–157 describes preparation of microcapsules of water-soluble drugs from an oil-in-oil (O/O) type emulsion wherein the internal phase is composed of a water-miscible solvent and the external phase contains silicone oil, vegetable oil and the like.

However, in preparation of microspheres by O/W type in-liquid drying process, the water-soluble drug take up into microspheres is insufficient and unsatisfactory. Further, O/O type in-liquid drying process has disadvantages. For example, it requires a large amount of solvent and heating at high temperature upon drying.

OBJECTS OF THE INVENTION

The main object of the present invention is to provide a process for producing microcapsules of a water-soluble drug by in-water drying process. This process improves the drug take up into microcapsules.

This object as well as other objects and advantages of the present invention will become apparent to those skilled in the art from the following description.

SUMMARY OF THE INVENTION

Under these circumstances, the present inventors have intensively studied to further increase the water-soluble drug take up into microcapsules. As a result, it has been found that the drug take up into microcapsules can be markedly improved by producing microcapsules of a water-soluble drug by in-water drying process in the presence of an osmotic pressure adjustor present in the external aqueous phase.

That is, according to the present invention, there is provided a process for producing microcapsules of a water-soluble drug by in-water drying process, which comprises carrying out the process in the presence of an osmotic pressure adjustor present in the external aqueous phase.

DETAILED DESCRIPTION OF THE INVENTION

According to the present invention, in the case of microencapsulation of a water-soluble drug by in-water drying process, it is possible to prevent distribution of the water-soluble drug to the aqueous phase (external phase), increase the water-soluble drug take up into microcapsules, and thereby increase the amount of the water-soluble drug within the microcapsules.

In the present invention, microcapsules are prepared by in-water drying process, preferably (W/O)/W type in-water drying process or O/W type in-water drying process. That is, in the case of the (W/O)/W type in-water drying process, microcapsules of a water-soluble drug are prepared by (1) preparing a W/O type emulsion whose internal aqueous phase is a solution containing a water-soluble drug and whose oil phase is a solution containing a polymer, (2) dispersing the W/O type emulsion in a solution or suspension for the aqueous phase containing an osmotic pressure adjustor to prepare an (W/O)/W type emulsion, and (3) subjecting the (W/O)/W type emulsion to in-water drying process to remove the solvent in the oil phase.

In the case of the O/W type in-water drying process, microcapsules of a water-soluble drug are prepared by (1) dispersing a solution or suspension for the oil phase comprised of the water-soluble drug and a polymer in a solution or suspension of the aqueous phase containing an osmotic pressure adjustor to prepare an O/W type emulsion, (2) subjecting the O/W type emulsion to in-water drying process to remove the solvent in the oil phase.

As examples of the water-soluble drug used in the present invention, there are water-soluble drug with high hydrophilicity and a small oil/water partition coefficient. The small oil/water partition coefficient means an octanol/water coefficient of not more than about 0.1.

The water-soluble drug is not specifically limited. Examples thereof include peptides having biological activities, other antibiotics, antitumor agents, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis inhibitors and the like.

Among them, peptides having biological activities, bone resorption inhibitors and angiogenesis inhibitors are preferred.

The peptides having biological activities to be used in the invention are those having two or more amino acids, preferably having molecular weight of about 200 to 80,000.

Examples of the peptide include luteinizing hormone-releasing hormone (LH-RH), its derivatives having similar activity, i.e., a peptide of the formula (I):

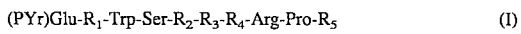

$(PYr)Glu-R_1-Trp-Ser-R_2-R_3-R_4-Arg-Pro-R_5$     (I)

wherein $R_1$ is His, Tyr, Trp or p-$NH_2$-Phe; $R_2$ is Tyr or Phe; $R_3$ is Gly or a D-amino acid residue; $R_4$ is Leu, Ile or Nle; $R_5$ is Gly-NH-$R_6$ (wherein $R_6$ is H or lower alkyl optionally substituted with hydroxy) or NH-$R_6$ (wherein $R_6$ is as defined above), or salts thereof [see, U.S. Pat. Nos. 3,853,837, 4,008,209, 3,972,859; G.B. Patent No. 1,423,083; and Proc. Nat. Acad. Sci. U.S.A., vol.78, pp. 6509–6512 (1981)].

As examples of the D-amino acid residue represented by $R_3$ in the above formula (I), there are α-D-amino acids having up to 9 carbon atoms (e.g., D-Leu, Ile, Nle, Val, Nval, Abu, Phe, Phg, Ser, Thr, Met, Ala, Trp, α-Aibu, etc.) and the like. These residues may have appropriate protecting groups (e.g., t-butyl, t-butoxy, t-butoxycarbonyl, etc.). The acid addition salts and metal complexes of the peptide (I) can be used in the same manner as the peptide (I).

The abbreviations of amino acids, peptides, protecting groups and the like in the peptide (I) are based on those established by IUPAC-IUB Commission on Biochemical Nomenclature or those commonly used in the art. When optical isomers of amino acids are present, the amino acids indicate L-isomers unless otherwise indicated.

The acetic acid salt of the peptide (I) wherein $R_1$ is His, $R_2$ is Tyr $R_3$ is D-Leu, $R_4$ is Leu and $R_5$ is $NHCH_2$—$CH_3$ is referred to as leuorotide acetate.

Other LH-RH analogues include nafarelin: (pyro)Glu-His-Trp-Ser-Tyr-(3-naphthyl)-D-Ala-Leu-Arg-Pro-GluNH$_2$, goserelin: (pyro)Glu-His-Trp-Ser-Tyr-O-tert-Butyl-D-Ser-Leu-Arg-Pro-semicarbazide or salts thereof. Other examples of the peptide having biological activities include LH-RH antagonists (see. U.S. Pat. Nos. 4,086,219, 4,124,577, 4,253,997, 4,317,815). Further, other examples of the peptide having biological activities include oligopeptides such as insulin, somatostatin, somatostatin derivatives (see, U.S. Pat. Nos. 4,087,290, 4,093,574, 4,100,117 and 4,253,998) growth hormone, prolactin, adrenocorzicotropic hormone (ACTH), melanocyte-stimulating hormone (MSH), thyrotropin-releasing hormone (TRH), their salts and derivatives (see, JP-A 50-121273, JP-A 52-116465), thyroid-stimulating hormone (TSH), luteinizing hormone (LH), follicle-stimulating hormone (FSH), vasopressin, vasopressin derivatives {desmopressin [see, Folia Endocrinologica Japonica, Vol. 54, No. 5, pp. 676–691 (1978)]}, oxytocin, calcitonin, parathyroid hormone, glucagon, gastrin, secretin, pancreozymin, cholecystokinin, angiotensin, human placental lactogen, human chorionic gonadotropin (HCG), enkephalin, enkephalin derivatives (see, U.S. Pat. No. 4,277,394 and EP-A 31,567); and polypeptides such as endorphin, kyotorphin, interferon (α-type, β-type, γ-type), interleukin (I to XI), tuftsin, thymopoietin, thymosin, thymosthymlin, thymic humoral factor (THF), serum thymic factor (FTS) and derivatives thereof (see, U.S. Pat. No. 4,229,438) and other thymic factors [Medicine in Progress, Vol. 125, No. 10, pp.835–843 (1983)], tumor necrosis factor (TNF), colony stimulating factor (CSF), motilin, dynorphin, bombesin, neurotensin, caerulein, bradykinin, urokinase, asparaginase, kallikrein, substance P, nerve growth factor, blood coagulation factor VIII and IX, lysozyme chloride, polymyxin B, colistin, gramicidin, bacitracin, protein synthesis-stimulating peptide (G.B. Patent No. 8,232,082), gastric inhibitory polypeptide (GIP), vasoactive intestinal polypeptide (VIP), platelet-derived growth factor (PDGF), growth hormone-releasing factor (GRF, somatoclinine), bone morphagenetic protein (BMP), epidermal growth hormone (EGF), erythropoietin (EPO) and the like.

As the peptide having biological activities, thyrotropin-releasing hormone (TRH) is preferred. Examples of the above antibiotics include gentamitin, dibekacin, kanendomycin, lividomycin, tzobramycin, amikacin, fradiomvcin, sisomicin, tetracycline hydrochloride, oxytetracvciine hydrocnloride, rolitetracycline, doxycycline hydrochloride, ampicillin, piperacillin, ticarcillin, cefalotin, cefaloridine, cefotiam, cefsulodin, cefmenoxime, cefmetazoie, cefazolin, cefotaxime, cefoperazone, ceftizoxime, moxolactam, thienamycin, sulfazecin, azusleonam and the like.

Examples of the above antitumor agents include bleomycin hydrochloride, methotrexate, actinomycin D, mitomycin C, vinblastine sulfate, vincristine sulfate, daunorubicin hydrochloride, adriamycin, neocarzinoszatin, cytosine arabinoside, fluorouracil, tetrahydrofuryl-5- fluorouracil krestin, picibanil, lentinan, levamisole, bestatin, azimexon, glycyrrhizin, poly I:C, poly A:U, poly ICLC, Cisolatin and the lake.

Examples of the above antipyretics, analgesics and anti-inflammatory agents include sodium salicylate, sulpyrine, sodium flufenamate, diclofenac sodium, indometacin sodium, morphine hydrochloride, pethidine hydrochloride, levorohanol tartarate, oxymorphone and the like.

Examples of the antitussive expectorants include ephedrine hydrochloride, methylephedrine hydrochloride, noscapine hydrochloride, codeine phosphate, dihydrocodeine phosphate, alloclamide hydrochloride, chlorphezianol hydrochloride, picoperidamine hydrochloride, cloperastine, protokylol hydrochloride, isoproterenol hydrochloride, salbutamol sulfate, terebutaline sulfate and the like.

Examples of the sedatives include chlorpromazine hydrochloride, prochlorperazine, trifluoperazine, atropine sulfate, methylscopolamine bromide and the like.

Examples of the muscle relaxants include pridinol methanesulfonate, tubocurarine chloride, pancuronium bromide and the like.

Examples of the antiepileptic agents include phenytoin sodium, ethosuximide, acetazolamide sodium, chlordiazepoxide hydrochloride and the like.

Examples of the antiulcer agents include metoclopramide, histidine hydrochloride and the like.

Examples of the antidepressants include imipramine, clomipramine, noxiptilin, phenelzine sulfate and the like.

Examples of the antiallergic agents include diphenhydramine hydrochloride, chlorpheniramine maleate, tripelennamine hydrochloride, methdilazine hydrochloride, clemizole hydrochloride, diphenylpyraline hydrochloride, methoxyphenamine hydrochloride and the like.

Examples of the cardiotonics include transbioxocamphor, theophyllol, aminophylline, etilefrine hydrochloride and the like.

Examples of the antiarrhythmic agents include propranololhydrochloride, alprenolol hydrochloride, bufetolol hydrochloride, oxyprenolol hydrochloride and the like.

Examples of the vasodilators include oxyfedrine hydrochloride, diltiazem hydrochloride, tolazoline hydrochloride, hexobendine, bamethan sulfate and the like.

Examples of the hypotensive diuretics include hexamethonium bromide, pentolinium, mecamylamine hydrochloride, ecarazine hydrochloride, clonidine hydrochloride and the like.

Examples of the antidiabetic agents include glymidine sodium, glipizide, phenformin hydrochloride, buformin hydrochloride, metformin and the like.

Examples of the anticoagulants include heparin sodium, sodium citrate and the like.

Examples of the hemostatics include thromboplastin, thrombin, menadione sodium bisulfite, acetomenaphthone, ε-aminocaproic acid, tranexamic acid, carbazochrome sodium sulfonate, adrenochrome monoaminoguanidine methanesulfonate and the like.

Examples of the antituberculous agents include isoniazid, ethambutol, sodium para-aminosalicylate and the like.

Examples of the hormone preparations include prednisolone succinate, predonisolone sodium phosphate, dexamethasone sodium sulfate, betamethasone sodiumphosphate, hexoestrol phosphate, hexoestrol acetate, methymazole and the like.

Examples of the narcotic antagonists include levallorphan tartarate, nalorphine hydrochloride, naloxone hydrochloride and the like.

Examples of the bone resorption inhibitors include (sulfur-containing alkyl)aminomethylenebisphosphonic acid and the like.

Examples of the angiogenesis inhibitors include angiostatic steroids [Science, 221, 719 (1983)], fumagillin (see, EP-A-325,199), fumagillol derivatives (see, EP-A-357,061, EP-A-359,036, EP-A-386,667, EP-A-415,294) and the like.

The drugs may be as they are or in the form of any possible pharmaceutical salts thereof including particular salts described above. When the drug has a basic group such as amino groups, it may form salts such as those with carbonic acid, hydrochloric acid, sulfuric acid, nitric acid, citric acid, maleic acid, tartaric acid, succinic acid, methanesulfonic acid or the like. When the drug has an acidic group such as a carboxyl group, it may form salts such as those with alkaline metals (e.g., sodium, potassium, etc.), organic amines (e.g., triethylamine, etc.) or basic amino acids (e.g., arginine, etc.).

The amount of the above water-soluble drug varies depending upon a particular kind of drug, desired pharmacological activities, duration time and the like. The concentration of the drug in the internal aqueous phase is about 0.001% to 90% (W/W), preferably about 0.01% to 80% (W/W), more preferably about 0.01% to 70% (W/W).

The polymer to be used in the present invention is a slightly water-soluble or water-insoluble polymer having biocompatiblity.

"Slightly water-soluble" means that solubility of the polymer in water is not more than about 1% (w/w).

Examples of the polymer in the present invention include biodegradable polymers such as poly fatty acid esters (e.g., polylactic acid, polyglycollic acid, polycitric acid, polymalic acid, etc.), poly-α-cyanoacrylic acid esters, poly-β-hydroxybutyric acid, polyalkylene oxalates (e.g., polytrimethylene oxalate, polytetramethylene oxalate, etc.), poly ortho esters, poly ortho carbonates and other polycarbonates (e.g., polyethylene carbonate, polyethylenepropylene carbonate, etc.), polyamino acids (e.g., poly-γ-benzyl-L-glutamic acid, poly-L-alanine, poly-γ-methyl-L-glutamic acid, etc.) and the like; biocompatible copolymers such as polystyrene, polymethacrylic acid, copolymer of acrylic acid and methacrylic acid, polyamino acids, dextran stearate, ethylcellulose, acetylcellulose, nitrocellulose, maleic anhydride copolymers, ethylene-vinylacetate copolymer, polyvinylacetate, polyacrylamide and the like. These polymers may be used alone or in combination thereof. They may be used in the form of a copolymer or mere mixture of these two or more polymers. They may be in the form of salts thereof.

Among these polymers, biodegradable polymers are preferred particulary for injections.

Preferred examples of the biodegradable polymers include polymers or copolymers of hydroxycarboxylic acids or mixtures thereof.

The hydroxycarboxylic acids are not specifically limited and preferred examples thereof include hydroxycarboxylic acids of the formula (II):

(II)

wherein R is hydrogen or an alkyl group.

As the alkyl group represented by R in the above formula, for example, straight-chain or branched-chain alkyl having 1 to 8 carbon atoms (e.g., methyl, ethyl, propyl, isopropyl, butyl, isobutyl, tert-butyl, pentyl, hexyl, heptyl, octyl, etc.) are preferred. Among them, straight-chain or branched-chain alkyl groups having 1 to 3 carbon atoms are particularly preferred.

As preferred examples of the above hydroxycarboxylic acids, there are glycollic acid, lactic acid, 2-hydroxybutyric acid, 2-hydroxyvaleric acid, 2-hydroxy-3-methylbutyric acid, 2-hydroxycaproic acid, 2-hydroxyisocaproic acid, 2-hydroxycaprylic acid and the like. Among them, glycolilc acid, lactic acid, 2-hydroxybutyric acid, 2-hydroxy-3-methylbutyric acid and 2-hydroxycaproic acid are more preferred. Further, glycollic acid, lactic acid and 2-hydroxybutyric acid are particularly preferred. When these hydroxycarboxylic acids exist as D-isomers, L-isomers or racemic mixtures thereof, any of them may be used. Preferably, racemic mixtures thereof are used.

The mode of copolymerization of the copolymers may be any of random, block and graft copolymerization. These glycollic acid copolymers are preferably those with relatively rapid biodegrability and the release period of not more than one month when used alone.

The polymers to be used in the present invention can be synthesized by general synthetic methods (see, e.g., JP-A 61-28521) without any problems.

The average molecular weight of the polymers to be used in the present invention is selected from the range of about 2,000 to 800,000, more preferably about 5,000 to 200,000.

When lactic acid/glycollic acid copolymer is used as the above polymer, the composition ratio is preferably about 100/0 to 50/50 (w/w). When butyric acid/glycollic acid copolymer is used, the composition ratio is preferably about 100/0 to 25/75 (w/w).

The weight-average molecular weight of lactic acid/glycollic acid copolymer is preferably about 5,000 to about 30,000, more preferably about 5,000 to 20,000.

When, for example, a mixture of polylactic acid (A) and glycollic acid/2-hydroxybutyric acid copolymer (B) is used as the above polymer, the mixing ratio represented by (A)/(B) is in the range of about 10/90 to about 90/10 (by weight), preferably about 25/75 to about 75/25 (by weight).

The weight-average molecular weight of polylactic acid is preferably about 5,000 to about 30,000, more preferably about 6,000 to about 20,000.

Preferably, the composition ratio of the glycollic acid/2-hydroxybutyric acid copolymer is about 40/60 to about 70/30 in terms of molar ratios. The weight-average molecular weight of glycollic acid/2-hydroxybutyric acid copolymer is preferably about 5,000 to about 25,000, more preferably about 5,000 to abut 20,000.

The molecular weight in the present specification means molecular weight in terms of polystyrene determined by gel permeation chromatography (GPC) using polystyrene as the standard material. The determination was carried out by using GPC column TSK gel (2000, 2500, 3000, manufactured by Toso, Japan) and using chloroform as the mobile phase.

The amount of the polymer to be used depends upon the strength of the pharmacological activity of the water-soluble drug, release rate and release period of the drug and the like. For example, the polymer is used as the microcapsule base in an amount of about 0.2 to 10,000 times, preferably about 1 to 1,000 times the weight of the water-soluble drug.

The concentration of the polymer in the oil phase is selected from the range of about 0.5 to 90% (w/w), preferbly about 2 to 60% (w/w).

As the osmotic pressure adjustor used in the invention, any material can be used so long as it produces osmotic pressure in an aqueous solution thereof.

Examples of the osmotic pressure adjustor include water-soluble polyhydric alcohols; water-soluble monohydric alcohols; water-soluble monosaccharides, disaccharides and oligosaccharides or their derivatives; water-soluble amino acids; water-soluble peptides, proteins or their derivatives and the like. Among them, water-soluble polyhydric alcohols; and water-soluble monosaccharides, disaccharides and oligosaccharides or their derivatives are preferred. Water-soluble polyhydric alcohols and water-soluble monosaccharides are more preferred. Water-soluble polyhydric alcohols are most preferred.

Examples of the above water-soluble polyhydric alcohols include dihydric alcohols (e.g., glycerin, etc.), pentahydric alcohols (e.g., arabitol, xylitol, adonitol, etc.), hexahydric alcohols (e.g., mannitol, sorbitol, dulcitol, etc.) and the like. Among them, hexahydric alcohols are preferred. In particular, mannitol is preferred.

Examples of the water-soluble monohydric alcohols include methanol, ethanol, isopropyl alcohol and the like. Among them, ethanol is preferred.

Examples of the above water-soluble monosaccharides include pentoses (e.g., arabinose, xylose, ribose, 2-deoxyribose, etc.) and hexoses (e.g., glucose, fructose, galactose, mannose, sorbose, rhamnose, fucose, etc.). Among them, hexoses are preferred.

Examples of the above water-soluble disaccharides include maltose, cellobiose, α,α-trehalose, lactose, sucrose and the like. Among them, lactose and sucrose are preferred.

Examples of the above water-soluble oligosaccharides include trisaccharides (e.g., maltotriose, raffinose, etc.) and tetrasaccharides (e.g., stachyose, etc.). Among them trisaccharides are preferred.

Examples of the derivatives of the above monosaccharides, disaccharides and oligosaccharides include glucosamine, galactosamine, glucuronic acid, galacturonic acid and the like.

Examples of the above water-soluble amino acids include neutral amino acids such as glycine, alanine, valine, leucine, isoleucine, phenylalanine, tyrosine, tryptophan, serine, threonine, proline, hydroxyproline, cysteine, methionine and the like; acidic amino acids such as aspartic acid, glutamic acid and the like; basic amino acids such as lysine, arginine, histidine and the like. There can also be used salts of these water-soluble amino acids with acids (e.g., hydrochloric acid, sulfuric acid, phosphoric acid, etc.) or alkalis (e.g., alkaline metals such as sodium, potassium and the like, etc.).

Examples of the water-soluble peptides, proteins or their derivatives include casein, globulin, prolamine, albumin, gelatin and the like.

These osmotic pressure adjustors can be used alone or in combination thereof. When the osmotic pressure adjustors are non-inonic materials, the concentration of these osmotic pressure adjustors in the external aqueous phase is about 0.001% to 60% (w/w), preferably about 0.01 to 40% (w/w), more preferably about 0.05 to 30% (w/w), particularly preferably about 1% (w/w). When the osmotic pressure adjustors are ionic materials, they are used in a concentration calculated by dividing the above concentration by the total ionic valency. The osmotic pressure adjustors may be added so that their concentration becomes more than their solubility, and a part of them may be dispersed.

The microcapsule preparation by (W/O)/W type in-water drying process in the present invention is carried out, for example, as follows.

First, a water-soluble drug is dissolved in water so that the concentration becomes the above concentration. If necessary, pharmaceutical carriers such as gelatin, agar, alginic acid, polyvinyl alcohol or basic amino acids can be added to the solution to obtain a solution or suspension for the internal aqueous phase.

As a pH adjustor to maintain the stability and solubility of biologically active peptides, for example, carbonic acid, acetic acid, oxalic acid, citric acid, phosphoric acid, hydrochloric acid, sodium hydroxide, arginine, lysine or their salts can be added to the solution or suspension for the inner aqueous phase. Further, as a stabilizer of biologically active peptides, there can be added, for example, albumin, gelatin, citric acid, sodium ethylenediaminetetraacetate, dextrin, sodium hydrogensulfite, polyols (e.g., polyethylene glycol, etc.) or the like. As a preservative of biologically active peptides, there can be added, for example, conventional paraoxybenzoic acid esters (e.g., methylparaben, propylparaben, etc.), benzyl alcohol, chlorobutanol, thimerosal or the like.

The solution or suspension for the internal aqueous phase thus obtained is added to a solution (oil phase) containing a polymer, followed by emulsification to prepare a W/O type emulsion. The emulsification can be carried out by conventional dispersion techniques such as intermittent shaking, mixing by means of a mixer (e.g., propeller agitator, turbine agitator, etc.), colloid mill operation, mechanical homogenization, ultrasonication or the like.

The above solution (oil phase) containing a polymer can be prepared by dissolving the polymer in an organic solvent. As the solvent, any solvent can be used so long as its boiling point is not more than about 120° C. and it is immiscible with water and capable of dissolving the polymer. Examples of the solvent include halogenated hydrocarbons (e.g., dichloromethane, chloroform, chloroethane, dichloroethane, trichloroethane, carbon tetrachloride, etc.), aliphatic acid esters (e.g., ethyl acetate, butyl acetate, etc.), ethers (e.g., ethyl ether, isopropyl ether, etc.), aromatic hydrocarbons (e.g., benzene, toluene, xylene, etc.) and the like. These solvents can be used alone or in combination thereof. A mixture thereof with a suitable mixing ratio can also be used.

Then a W/O type emulsion thus prepared is subjected to in-water drying process in an aqueous phase containing an osmotic pressure adjustor in the above concentration. That is, the W/O type emulsion is added to the third phase (aqueous phase) further containing an osmotic pressure adjustor to form a (W/O)/W type three-phase emulsion, followed by removal of the solvent in the oil phase to prepare microcapsules.

The preparation of microcapsules by O/W type in-water drying process in the present invention can be carried out, for example, as follows.

First, a polymer is dissolved in a water-insoluble solvent. Then a water-soluble drug is added to the solution and they are mixed well to prepare an oil phase. In this case, it is advantageous to optionally use a water-soluble solvent together with a water-insoluble solvent.

Then, the oil phase thus prepared is subjected to in-water drying process in an aqueous phase containing an osmotic pressure adjustor in the above concentration. That is, the oil phase is added to the second phase (aqueous phase) further containing an osmotic pressure adjustor to forman O/W type emulsion, followed by removal of the solvent in the oil phase to prepare microcapsules.

As the above water-insoluble solvent, any water-insoluble solvent can be used. Examples of the water-insoluble solvent include halogenated hydrocarbons (e.g., dichloromethane, chloroform, dichlorohexane, chloroethane, dichloroethane, trichloroethane, carbon tetrachloride, etc.), esters (e.g., ethyl acetate, etc.), ethers (e.g., ethyl ether, etc.), aromatic hydrocarbons (e.g., benzene, toluene, etc.), hydrocarbons (e.g., n-pentane, n-hexane, etc.) and the like.

As the above water-soluble solvent, any solvent can be used so long as it is water-soluble and miscible with the above water-insoluble solvent. Examples of the water-soluble solvent include alcohols (e.g., methanol, ethanol, propyl alcohol, isopropyl alcohol, etc.), acetone, acetonitrile and the like.

An emulsifying agent can be added to the third phase (aqueous phase) in (W/O)/W type in-water drying process or the second phase (aqueous phase) in O/W type drying process. As the above emulsifying agent, any emulsifying agent can be used so long as it generally forms stable O/W type emulsions. Examples thereof include anionic surfactants (e.g., sodium oleate, sodium stearate, sodium laurate, etc.); nonionic surfactants such as polyoxyethylenesorbitan aliphatic acid esters (e.g., Tween 80, Tween 60 (Atlas Powder Co.), etc.), polyoxyethylene castor oil derivatives (e.g., HCO-60, HCO-50 (Nikko Chemicals), etc.), polyvinyl pyrrolidone, polyvinyl alcohol, carboxymethyl cellulose, lecithin, gelatin and the like. These emulsifying agents can be used alone or in combination thereof. They are used in a concentration appropriately selected from the range of about 0.01% to 20% (W/W), preferably about 0.05% to 10% (W/W).

The removal of the solvent in the oil phase can be carried out by conventional methods. For example, it is carried out by stirring with a propeller-type stirrer, magnetic stirrer or the like under atmospheric pressure or gradually reducing pressure, or while controlling degree of vacuum by using a rotary evaporator or the like. In this case, at the time when solidification of the polymer proceeds in some degree and the loss caused by the release of the drug from the internal phase is decreased, a (W/O)/W type or O/W type emulsion may be warmed gradually to remove the solvent more completely, which results in saving of the required time. Alternatively, when thickening and solidification are carried out by methods other than those based on temperature, the removal can be carried out by merely allowing the (W/O)/W type or O/W type emulsion to stand with stirring, by warming it or by spraying nitrogen gas or the like. This removal step of the solvent is of importance and greately influences the surface structure of microcapsules controlling the release of the drug. For example, rapid removal produces a number of pores on the surface or makes pores larger in their size, which results in increased release rate of the drug.

Microcapsules thus obtained are collected by centrifugation or filtration. Then free water-soluble drug, carriers for the drug, or the like attached onto the surface of the microcapsules is washed with distilled water repeatedly several times water in the microcapsules and the solvent in the microcapsule preparation are dried in reduced pressure more completely, if necessary, with warming.

The microcapsules thus obtained are screened, if necessary after light pulverization, to remove too large microcapsules. The microcapsule size varies depending upon the desired degree of prolonged release. When the microcapsules are used as suspensions, the microcapsule size can be in the range which satisfies their dispersibility and needle pass requirements. For example, the average diameter is preferably in the range of about 0.5 to 400 µm, more preferably about 2 to 200 µm.

The microcapsules prepared according to the process of the present invention can readily be administered as they are as injections or implants intramuscularly, subcutaneously, or into blood vessels, organs, cava articulare or foci such as tumor. Further, they can be administered in the form of various preparations. They can also be used as raw materials in the production of various preparations.

As examples of the above preparations, there are injections, oral preparations (e.g., powders, granules, capsules, tablets, etc.), nasal preparations, suppositories (e.g., rectal suppositories, vaginal suppositories, etc.) and the like.

When the microcapsules according to the present invention are to be processed into injections, the microcapsules are dispersed in an aqueous vehicle together with a dispersing agent (e.g., Tween 80, HCO-60 (manufactured by Nikko Chemicals), carboxymethylcellulose, sodium alginate, etc.), a preservative (e.g., methylparaben, propylparaben, benzyl alcohol, chlorobutanol, etc.), a tonicity agent (e.g., sodium chloride, glycerin, sorbitol, glucose, etc.) and the like to prepare aqueous suspensions. They may also be dispersed in a vegetable oil (e.g., olive oil, sesame oil, peanut oil, cottonseed oil, corn oil, etc.), propylene glycol or the like to prepare oily suspensions. In this manner, prolonged release injections can be prepared.

Alternatively, excipients (e.g., mannitol, sorbitol, lactose, glucose, etc.) may be added, in addition to the above components, to the above prolonged release injections of microcapsules in the form of suspensions. After redispersion, the injections are solidified by freeze drying or spray drying, and distilled water for injection or an appropriate disperser may be added just before use. In this manner, more stable prolonged release injections can be obtained.

When the microcapsules according to the present invention are to be processed into, for example, tablets, in general, they can be prepared according to conventional preparation methods. For example, there can be added an excipients (e.g., lactose, crystalline cellulose, sucrose, starch such as corn starch, etc.), disintegrating agent (e.g., starch such as corn starch, croscarmellose sodium, carboxymethylstarch sodium, calcium carbonate, etc.), binder (e.g., crystalline cellulose, acacia, dextrin, carboxymethylcellulose, polyvinyl pyrrolidone, hydroxypropylcellulose, etc.) or lubricant (e.g., talc, magnesium stearate, polyethylene glycol 6000, etc.) and the like. Then the mixture is compressed for molding.

When the microcapsules of the present invention are processed to, for example, nasal preparations, they are molded into the form of solid, semisolid or liquid. In any case, conventional preparation methods can be used. To prepare the above solid nasal preparations, the mirocapsules either as they are or together with an excipient (e.g., glucose, mannitol, starch, microcrystalline cellulose, etc.), thickener (e.g., natural gum, cellulose derivatives, polyacrylates, etc.) are processed into powdery compositions. To make liquid compositions, the microcapsules are processed into an oily or aqueous suspension in substantially the same manner as in injections. The semi-solid preparation may be aqueous or oily gels or ointments. In any case, there may be added a pH adjustor (e.g., carbonic acid, phosphoric acid, citric acid, hydrochloric acid, sodium hydroxide, etc.), preservative (e.g., p-hydroxybenzoic acid esters, chlorobutanol, benzalkonium chloride, etc.) and the like.

When the microcapsules of the present invention are processed to suppositories, they can be prepared per se known methods in the form of oily or aqueous solid, semi-solid or liquid. The oleaginous bases for the above composition are not specifically limited so long as they do not dissolve the microcapsules. Examples thereof include higher fatty acid glycerides [e.g., cacao butter, Witepsol (Dynamit-Nobel, Germany), etc.], intermediate fatty acids [e.g., Miglyol (Dynamit-Nobel), etc.], vegetable oils (e.g., sesame oil, soybean oil, cottonseed oil, etc.) and the like. As examples of the aqueous bases, there are polyethylene glycol and propylene glycol. As examples of the aqueous gels, there are natural gum, cellulose derivatives, vinyl polymers, polyacrylates and the like.

The prolonged release preparations of the microcapsules according to the present invention have low toxicity and can be used safely.

The dosage of the preparations according to the present invention varies depending upon the kind and amount of water-soluble drugs as active ingredients, dosage forms, duration of drug release, recipient animals (e.g., warm-blooded mammals such as mice, rats, horses, cattle, humans, etc.) and objects of treatment. It is, however, sufficient to ensure that the effective dose of the active ingredient will be administered. For example, the unit dose for adults (body weight: 50 kg) may be selected from the range of about 1 mg to 10 g, preferably about 10 mg to 2 g in terms of the weight of the microcapsules. In the case of administration as the above injections, the volume of the suspension can be selected from the range of about 0.1 to 5 ml, preferably about 0.5 to 3 ml.

According to the present invention, in the preparation of microcapsules of a water-soluble drug by in-water drying process, the water-soluble drug take up into the microcapsules and the water-soluble drug content in the microcapsules can be increased. Thus, there is provided a pharmaceutical composition prepared as the microcapsules which comprises an effective amount of a water-soluble drug in a larger amount than conventional unit dose and a biocompatible polymer, said microcapsules being capable of prolonged release of the drug over a long period and having a small initial burst of a drug.

The following examples further illustrate the present invention in detail but are not to be construed to limit the scope thereof. In the examples, all the percents (%) are indicated as weight/weight percents, and all the molecular weight are indicated as weight-average molecular weight.

The drug take up (%) shown in the examples was calculated from the following formula:

$$\text{Drug take up (\%)} = 100 \times \frac{\text{The amount of the drug in the microcapsules}}{\text{The initial amount of the drug added}}$$

EXAMPLE 1

Thyrotropin-releasing hormone (TRH) (0.5 g) was dissolved in water (0.2 g). To this solution was added a solution containing lactic acid/glycollic acid copolymer (PLGA, lactic acid/glycolic acid=75/25 (W/W), molecular weight: 14,000)(4.5 g) in dichloromethane (4.9 ml) to prepare a W/O emulsion. This W/O emulsion was cooled to 19° to 20° C. and dispersed in 0.1% polyvinyl alcohol (PVA) solution (1 liter) containing 1% mannitol previously cooled to 19° to 20° C. to prepare a (W/O)/W emulsion. After in-water drying for 3 hours, the microcapsules were collected by centrifugation and dried. The TRH take up into the microcapsules was 90.3%, and the TRH content in the microcapsules was 8.0%, both of which were higher than in Comparative Example 1.

EXAMPLE 2

TRH (0.5 g) was dissolved in water (0.3 g). To this solution was added a solution of PLGA (lactic acid/glycollic acid=75/25 (W/W), molecular weight: 14,000) (4.5 g) in dichloromethane (5.6 ml) to prepare a W/O emulsion. This W/O emulsion was cooled to 19° to 20° C. According to the same manner as that described in Example 1, microcapsules were prepared using 0.1% PVA solution (1 liter) containing 5% mannitol previously cooled to 19° to 20° C. The TRH take up into the microcapsules was 83.4%, and the TRH content in the microcapsules was 7.4%, both of which were higher than in Comparative Example 1.

EXAMPLE 3

According to the same manner as that described in Example 1, microcapsules were prepared using 0.1% PVA solution containing 10% mannitol. The TRH take up into the microcapsules was 82.8%, and the TRH content in the microcapsules was 7.4%, both of which were higher than in Comparative Example 1.

EXAMPLE 4

According to the same manner as that described in Example 1, microcapsules were prepared using 0.1% PVA solution containing 0.5% mannitol. The TRH take up into the microcapsules was 88.3%, and the TRH content in the microcapsules was 7.9%, both of which were higher than in Comparative Example 1.

EXAMPLE 5

TRH (15 g) was dissolved in water (6 g). To this solution was added a solution of PLGA (lactic acid/glycollic acid =75/25 (W/W), molecular weight: 14,000) (135 g) in dichloromethane (168 ml) to prepare a W/O emulsion. This emulsion was cooled to 19° to 20° C. and dispersed in 0.1% PVA solution (45 liters) containing 1% mannitol previously cooled to 19° to 20° C. to prepare a (W/O)/W emulsion. After in-water drying for 3 hours, the microcapsules were collected by centrifugation and dried. The TRH take up into the microcapsules was 93.9%, and the TRH content in the microcapsules was 8.3%, both of which were higher than in Comparative Example 2.

EXAMPLE 6

According to the same manner as that described in Example 1, microcapsules were prepared using 0.1% PVA solution containing 1% glucose. The TRH take up into the microcapsules was improved and the TRH content in the microcapsules was increased in comparison with Comparative Example 1.

EXAMPLE 7

According to the same manner as that described in Example 1, microcapsules were prepared using 0.1% PVA solution containing 0.2% NaCl. The TRH take up into the microcapsules was 95.2%, and the TRH content in the microcapsules was 7.9%, both of which were higher than in Comparative Example 1.

EXAMPLE 8

Leuprolide acetate (495 mg) and gelatin (80 mg) were dissolved in water (0.5 g). To this solution was added a solution of PLGA (lactic acid/glycollic acid=75/25 (W/W), molecular weight: 14,000) (3.97 g) in dichloromethane (5.5 ml) to prepare a W/O emulsion. This emulsion was cooled to 18.5° C. and dispersed in 0.1% PVA solution (1 liter) containing 1% mannitol previously cooled to 18.5° C. to prepare a (W/O)/W emulsion. After in-water drying for 3 hours, the microcapsules were collected by centrifugation and freeze-dried. The lueprolide acetate take up into the microcapsules was 89.1%, and the leuprolide acetate content in the microcapsules was 9.7%, both of which were higher than in Comparative Example 3.

EXAMPLE 9

TRH (22.5 g) was dissolved in water (6.75 g). To this solution was added a solution of PLGA (lactic acid/glycollic acid=75/25 (W/W), molecular weight: 14,000) (202.5 g) in dichloromethane (252 ml) to prepare a W/O emulsion. This emulsion was cooled to 14° to 16° C. and dispersed in 0.1% PVA solution (45 liter) containing 1% mannitol previously cooled to 14° to 16° C. to prepare a (W/O)/W emulsion. After in-water drying for 3 hours, the microcapsules were collected by centrifugation and dried. The TRH take up into the microcapsules was 88%, and the TRH content in the microcapsules was 7.5%, both of which were higher than in Comparative Example 2.

EXAMPLE 10

TRH (67.5 g) was dissolved in water (20.25 g). To this solution was added a solution of PLGA (lactic acid/glycollic acid=75/25 (W/W), molecular weight: 14,000) (607.5 g) in dichloromethane (756 ml) to prepare a W/O emulsion. This W/O emulsion was cooled to 14° to 16° C. According to the same manner as that described in Example 9, microcapsules were prepared using 0.1% PVA solution (135 liter) containing 1% mannitol previously cooled to 14° to 16° C. The TRH take up into the microcapsules and the TRH content in the microcapsules were higher than in Comparative Example 2.

Comparative Example 1

To an aqueous solution containing TRH (0.5 g) was added a solution of PLGA (lactic acid/glycollic acid=75/25 (W/W), molecular weight: 14,000) (4.5 g) in dichloromethane (5.6 ml) to prepare a W/O emulsion. This emulsion was cooled to 19° to 20° C. and dispersed in 0.1% PVA solution (1 liter) previously cooled to 19° to 20° C. to prepare a (W/O)/W emulsion. After in-water drying for 3 hours, the microcapsules were collected by centrifugation and dried. The TRH take up into the microcapsules was 76.6%, and the TRH content in the microcapsules was 6.8%.

Comparative Example 2

TRH (15 g) was dissolved in water (9 g). To this solution was added a solution of PLGA (lactic acid/glycollic acid =75/25 (W/W), molecular weight: 14,000) (135 g) in dichloromethane (168 ml) to prepare a W/O emulsion. This emulsion was cooled to 19° to 20° C. and dispersed in 0.1% PVA solution (45 liters) previously cooled to 19° to 20° C. to prepare a (W/O)/W emulsion. After in-water drying for 3 hours, the microcapsules were collected by centrifugation and dried. The TRH take up into the microcapsules was 76.0%, and the TRH content in the microcapsules was 6.5%.

Comparative Example 3

Leuprolide acetate (16.5 g) and gelatin (2.7 g) were dissolved in water (16.7 g). To this solution was added a solution of PLGA (lactic acid/glycollic acid=75/25 (W/W), molecular weight: 14,000) (132.3 g) in dichloromethane (167 ml) to prepare a W/O emulsion. This emulsion was cooled to 18.5° C. and dispersed in 0.1% PVA solution (25 liters) previously cooled to 18.5° C. to prepare a (W/O)/W emulsion. After in water drying for 3 hours, the microcapsules were collected by centrifugation and freeze-dried. The TRH take up into the microcapsules was 85.3%, and the leuprolide acetate content in the microcapsules was 9.3%.

What is claimed is:

1. A process for producing microcapsules of a water-soluble drug by in-water drying process, which comprises carrying out the process in the presence of an osmotic pressure adjustor present in the external aqueous phase, wherein the concentration of the osmotic pressure adjustor in the external aqueous phase is about 0.001 to about 60% (w/w), and wherein the osmotic pressure adjustor is selected from the group consisting of water-soluble polyhydric alcohols, water-soluble monohydric alcohols, water-soluble monosaccharides, water-soluble disaccharides, water-soluble oligosaccharides and their derivatives, and water-soluble amino acids and their salts.

2. A process according claim 1 which comprises (1) preparing a W/O emulsion whose internal aqueous phase is a solution containing a water-soluble drug and whose oil phase is a solution containing a polymer, (2) dispersing the W/O emulsion in a solution or suspension for the aqueous phase containing an osmotic pressure adjustor to prepare a (W/O)/W emulsion, and (3) subjecting the (W/O)/W emulsion to in-water drying process.

3. A process according to claim 1 which comprises (1) dispersing a solution or suspension for the oil phase comprising a water-soluble drug and a polymer in a solution or suspension for the aqueous phase containing an osmotic pressure adjustor to prepare an O/W emulsion, and (2) subjecting the O/W emulsion to in-water drying process.

4. A process according to claim 1 wherein the water-soluble drug is a peptide having biological activities.

5. A process according to claim 4, wherein the molecular weight of the polypeptide is about 200 to about 80,000 daltons.

6. A process according to claim 4 wherein the peptide having biological activities is thyrotropin-releasing hormone.

7. A process according to claim 1 wherein the osmotic pressure adjustor is a water-soluble polyhydric alcohol.

8. A process according to claim 1 wherein the osmotic pressure adjustor is a water-soluble hexahydric alcohol.

9. A process according to claim 1 wherein the osmotic pressure adjustor is mannitol.

10. A process according to claim 1 wherein the concentration of the osmotic pressure adjustor in the external aqueous phase is about 0.05 to about 30% (w/w).

11. A process according to claim 10 wherein the concentration of the osmotic pressure adjustor in the external aqueous phase is about 1% (w/w).

12. A process according to claim 2, wherein the weight-average molecular weight of the polymer is about 2,000 to about 800,000 daltons as determined by gel permeation chromatography.

13. A process according to claim 2 wherein the polymer is a biodegradable polymer.

14. A process according to claim 13 wherein the biodegradable polymer is a polymer or a copolymer of hydroxycarboxylic acids, or mixtures thereof.

15. A process according to claim 2 wherein the polymer is lactic acid/glycollic acid copolymer.

16. A process according to claim 1, wherein the osmotic pressure adjustor is one or more water-soluble polyhydric alcohol and derivatives thereof.

17. A process according to claim 1, wherein the osmotic pressure adjustor is one or more water-soluble monohydric alcohol and derivatives thereof.

18. A process according to claim 1, wherein the osmotic pressure adjustor is one or more water-soluble monosaccharide and derivatives thereof.

19. A process according to claim 1, wherein the osmotic pressure adjustor is one or more water-soluble disaccharide and derivatives thereof.

20. A process according to claim 1, wherein the osmotic pressure adjustor is one or more water-soluble oligosaccharide and derivatives thereof.

21. A process according to claim 1, wherein the osmotic pressure adjustor is one or more water-soluble amino acid and salts thereof.

* * * * *

UNITED STATES PATENT AND TRADEMARK OFFICE
CERTIFICATE OF CORRECTION

PATENT NO. : 5,611,971
DATED : March 18, 1997
INVENTOR(S) : Koichi MAEDERA et al.

Page 1 of 2

It is certified that error appears in the above-identified patent and that said Letters Patent is hereby corrected as shown below:

Column 1, line 24, "dissolving" should read --(1) dissolving--.

Column 3, line 15, "leuorotide" should read --leuprolide--;

line 18, "Bu" should read --bu- --;

line 25, "4,087,290" should read --4,087,390--;

line 26, "adrenocorzicotropic" should read --adrenocorticotropic--;

line 58, "gentamitin" should read --gentamicin--;

line 59, "tzobramycin" should read --tobramycin--;

line 59, "fradiomvcin" should read --fradiomycin--;

line 60, "oxytetracvciine" should read --oxytetracycline--;

UNITED STATES PATENT AND TRADEMARK OFFICE
CERTIFICATE OF CORRECTION

PATENT NO. : 5,611,971
DATED : March 18, 1997
INVENTOR(S) : Koichi MAEDERA et al.

It is certified that error appears in the above-identified patent and that said Letters Patent is hereby corrected as shown below:

line 61, "hydrocnloride" should read --hydrochloride--;

line 63, "cefmetazoie" should read --cefmetazole--.

Column 4, line 2, "neocarzinoszatin" should read --neocarzinostatin--;

line 5, "Cisolatin" should read --Cisplatin--;

line 6, "lake" should read --like-- line 11, "levorohanol" should read --levorphanol--;

Column 13, line 58, "TRH" should read --leuprolide acetate--.

Signed and Sealed this

Twenty-fourth Day of February, 1998

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,611,971
DATED : March 18, 1997
INVENTOR(S) : Koichi MAEDERA et al.

It is certified that error appears in the above-identified patent and that said Letters Patent is hereby corrected as shown below:

Please amend the following Claim:

Claim 5, line 2, "polypeptide" should read --peptide--.

Signed and Sealed this

Twenty-fourth Day of March, 1998

Attest:

BRUCE LEHMAN

Attesting Officer    Commissioner of Patents and Trademarks